United States Patent
Perlemoine et al.

(10) Patent No.: US 12,275,980 B2
(45) Date of Patent: Apr. 15, 2025

(54) METHOD FOR DETERMINING THE SENSITIVITY OF A BACTERIAL STRAIN TO A BACTERIOPHAGE

(71) Applicants: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE GRENOBLE ALPES, Saint Martin d'heres (FR)

(72) Inventors: Prisca Perlemoine, Grenoble (FR); Thomas Bordy, Grenoble (FR); Pierre Marcoux, Grenoble (FR); Emmanuel Picard, Grenoble (FR); Rémi Toutain, Grenoble (FR); Marc Zelsmann, Biviers (FR); Alexis Maire, Granges-Narboz (FR)

(73) Assignees: COMMISSARIAT A L'ENERGIE ATOMIQUE ET AUX ENERGIES ALTERNATIVES, Paris (FR); CENTRE NATIONAL DE LA RECHERCHE SCIENTIFIQUE, Paris (FR); UNIVERSITE GRENOBLE ALPES, Saint Martin d'heres (FR)

( * ) Notice: Subject to any disclaimer, the term of this patent is extended or adjusted under 35 U.S.C. 154(b) by 888 days.

(21) Appl. No.: 17/097,687

(22) Filed: Nov. 13, 2020

(65) Prior Publication Data
US 2021/0147899 A1    May 20, 2021

(30) Foreign Application Priority Data
Nov. 15, 2019   (FR) ..................... 19 12804

(51) Int. Cl.
C12Q 1/18    (2006.01)
C12Q 1/70    (2006.01)

(52) U.S. Cl.
CPC ............... *C12Q 1/18* (2013.01); *C12Q 1/70* (2013.01)

(58) Field of Classification Search
None
See application file for complete search history.

(56) References Cited

U.S. PATENT DOCUMENTS

| 2008/0193418 | A1* | 8/2008 | Walter ............... A61K 51/1203 |
| | | | 435/235.1 |
| 2009/0081173 | A1* | 3/2009 | Serwer ................. A61K 35/744 |
| | | | 435/235.1 |
| 2011/0129814 | A1  | 6/2011 | Aljaro et al. |
| 2014/0133702 | A1* | 5/2014 | Zheng .................... B01L 3/508 |
| | | | 382/103 |
| 2014/0220659 | A1  | 8/2014 | Dastych et al. |
| 2017/0035077 | A1  | 2/2017 | Dastych et al. |
| 2020/0157644 | A1  | 5/2020 | Rames |

FOREIGN PATENT DOCUMENTS

| EP | 2 261 379 A1 | 12/2010 |
| EP | 2 747 578 A1 | 7/2014 |
| WO | WO 2019/018886 A1 | 1/2019 |

OTHER PUBLICATIONS

Han C, Yang C. Viral plaque analysis on a wide field-of-view, time-lapse, on-chip imaging platform. Analyst. Aug. 7, 2014;139(15):3727-34. doi: 10.1039/c3an02323k. PMID: 24611157; PMCID: PMC4077935. (Year: 2014).*
Babic, J., Griscom, L., Cramer, J. et al. An easy-to-build and re-usable microfluidic system for live-cell imaging. BMC Cell Biol 19, 8 (2018). https://doi.org/10.1186/s12860-018-0158-z (Year: 2018).*
French Preliminary Search Report issued Jul. 28, 2020 in French Application 19 12804 filed Nov. 15, 2019 (with English Translation of Categories of Cited Documents and Written Opinion), 14 pages.
Henry, M. et al., "Development of a high throughput assay for indirectly measuring phage growth using the OmniLog™ system," Bacteriophage, vol. 2, No. 3, Jul. 2012, XP0055717274, 10 pages.
Estrella, L. A. et al., "Characterization of novel *Staphylococcus aureus* lytic phage and defining their combinatorial virulence using the OmniLog™ system," Bacteriophage, vol. 6, No. 3, Jul. 2016, XP055717278, 14 pages.
Perlemoine, P. et al., "Phage susceptibility testing with lensless imaging technique (Conference Presentation)," Photonic Diagnosis, Monitoring, Prevention, and Treatment of Infections and Inflammatory Diseases 2020, Mar. 10, 2020, (submitting Abstract only), XP055715784, 2 pages.

* cited by examiner

Primary Examiner — Stacy B Chen
(74) Attorney, Agent, or Firm — Oblon, McClelland, Maier & Neustadt, L.L.P.

(57) ABSTRACT

Method for determining the sensitivity of a bacterial strain of interest to a viral strain of bacteriophages, the method comprising:
  a) preparing a sample, this comprising bringing bacteria, belonging to the bacterial strain of interest, into contact with bacteriophages, each bacteriophage belonging to the same viral strain, the bacteria being either in a liquid medium, or in an agar medium;
  b) placing the sample between a light source and an image sensor, the light source emitting a light wave in an emission spectral band comprised between 500 nm and 600 nm;
  c) illuminating the sample using the light source and acquiring at least one image of the sample, with the image sensor, in the emission spectral band, no image-forming optic being placed between the sample and the image sensor;
  d) on the basis of the acquired images, determining a sensitivity of the bacterial strain of interest to the viral strain.

16 Claims, 11 Drawing Sheets

METHOD FOR DETERMINING THE SENSITIVITY OF A BACTERIAL STRAIN TO A BACTERIOPHAGE

TECHNICAL FIELD

The technical field of the invention is the characterization of the susceptibility of a bacterial strain to be infected, then lysed, by a bacteriophage.

PRIOR ART

Phage therapy is the use of bacteriophages, usually called phages, to treat infections of bacterial origin. It is a question of applying lytic phages, which are capable of infecting certain bacteria, then of lysing them. It is a relatively old treatment, discovered and practised before the emergence of antibiotics. However, in most countries, this type of treatment has been rather neglected, to the benefit of use of antibiotics. At the present time, phage therapy is considered a promising therapeutic approach for treating certain bacterial infections, and one that is particularly suitable when the bacteria are resistant to antibiotics.

The effectiveness of phage therapy has been demonstrated for the treatment of infections by bacteria such as *Pseudomonas aeruginosa, Escherichia coli*, and *Staphilococcus Aureus*, in applications such as skin grafts for large burns or pathologies related to diabetes.

The phages used in phage-therapy applications are lytic phages, such that, when a bacterium has been infected by a phage, the latter is lysed. The lysis results from the production of endolysins. During an infection, the metabolism of the bacterium leads to a replication of the number of phages, which take the form of virions. The latter are freed following the lysis of the bacterium. An infection is therefore followed by an increase in the number of phages able to infect, then lyse, other bacteria. Bacterial proliferation is decreased or even stopped thereby.

In order to test the sensitivity of a bacterium to a phage, trials, usually denoted by the term "phagrogram", are carried out in the laboratory. It is a question of testing the susceptibility of a bacterial strain to be infected, then lysed, by a phage. However, these trials require various viral strains to be tested with various ratios of numbers of phages/bacteria. The number of viral strains may be comprised between 5 and 100, whereas 5 to 10 ratios of numbers of phages/bacteria are generally tested for each viral strain. The number of trials to be carried out is therefore high.

The inventors provide a simple method allowing the sensitivity of a bacterial strain to a viral strain to be analysed. The method allows the development of bacteria to be tracked and bacterial lysis by phages to be detected early on. It is also able to handle, simultaneously, a plurality of combinations of numbers of phages, optionally of various viral strains, and of numbers of bacteria, optionally of various bacterial strains. The objective is to decrease the time taken to detect the sensitivity of a bacterial strain to a viral strain.

SUMMARY OF THE INVENTION

One subject of the invention is a method for determining the sensitivity of a bacterial strain to a viral strain of bacteriophages, the method comprising:
a) preparing a sample, this comprising bringing bacteria, of the bacterial strain, into contact with bacteriophages, each bacteriophage belonging to the same viral strain, the bacteria being either in a liquid medium, or in an agar medium;
b) placing the sample between a light source and an image sensor, the light source emitting a light wave in an emission spectral band preferably comprised between 500 nm and 600 nm;
c) illuminating the sample using the light source and acquiring at least one image of the sample, with the image sensor, in the emission spectral band, no image-forming optic preferably being placed between the sample and the image sensor;
d) on the basis of each acquired image, determining a sensitivity of the bacterial strain to the viral strain of the bacteriophages.

The width of the spectral emission band is preferably narrower than 100 nm or 50 nm. The distance between the sample and the image sensor is preferably smaller than 5 cm or smaller than 1 cm.

According to one embodiment:
in step a), the bacteria and the bacteriophages are mixed in an aqueous solution;
step c) comprises acquiring at least two images, at successive measurement times;
step d) comprises determining a light intensity detected by all or part of the image sensor, in each image respectively acquired at each measurement time, such that the bacterial strain is considered to be:
hardly or not sensitive to the viral strain of the bacteriophages when the detected light intensity decreases between two successive measurement times;
or sensitive to the viral strain of the bacteriophages when the detected light intensity does not decrease or increases between two successive measurement times.

Step d) may comprise determining an attenuation of the light, emitted by the light source, by the sample, such that the bacterial strain is considered to be:
hardly or not sensitive to the viral strain of the bacteriophages when the attenuation increases between two successive measurement times;
or sensitive to the viral strain of the bacteriophages when the attenuation does not increase between two successive measurement times.

According to one embodiment:
in step a), the bacteria and the bacteriophages are mixed in an aqueous solution;
step c) comprises acquiring at least two images, at successive measurement times;
step d) comprises determining a texture descriptor for each acquired image, such that the bacterial strain is considered to be:
hardly or not sensitive to the viral strain of the bacteriophages when the variation in the texture descriptor is indicative of an increase in scattering of the light by the sample between two successive measurement times;
or sensitive to the viral strain of the bacteriophages when the variation in the texture descriptor is indicative of a decrease or a stagnation in scattering of the light by the sample between two successive measurement times.

The texture descriptor may be determined for one or more regions of interest of the image.

According to one embodiment:
in step a), the bacteria and the bacteriophages are mixed in an agar medium;

step c) comprises acquiring at least one image, subsequently to step a);

step d) comprises analysing each acquired image, so as to identify light regions of interest, each light region of interest corresponding to an infection of bacteria by bacteriophages, forming a viral plaque, each light region of interest indicating a sensitivity of the bacterial strain to the viral strain of the bacteriophages.

The method may then include:

counting the number of light regions of interest in at least one acquired image;

estimating a viral load of the bacteriophages in the sample on the basis of the number of light regions of interest counted.

According to one embodiment:

in step a), the bacteria are located in an agar medium, and the bacteriophages are located in a solution, step a) comprising depositing at least one droplet of the solution on the agar medium;

step c) comprises acquiring at least one image, subsequently to step a);

step d) comprises analysing each acquired image, so as to identify light regions of interest, each light region of interest corresponding to an infection of bacteria by bacteriophages, forming a viral plaque, such that the appearance of each light region of interest indicates a sensitivity of the bacterial strain to the viral strain of the bacteriophages.

Step a) may comprise depositing a plurality of droplets, the droplets being spaced apart from one another, two different droplets respectively comprising:

bacteriophages of various viral strains;

and/or various concentrations of bacteriophages of a given viral strain.

According to one embodiment:

in step a), the bacteriophages are located in an agar medium, and the bacteria are located in a solution, step a) comprising depositing a droplet of the solution on the agar medium;

step c) comprises acquiring at least one image, subsequently to step a);

step d) comprises analysing each acquired image, so as to identify:

light regions of interest, each light region of interest corresponding to an infection of bacteria by bacteriophages, such that each light region of interest indicates a sensitivity of the bacterial strain to the viral strain of the bacteriophages;

or dark regions of interest, each dark region of interest corresponding to a development of bacteria in the presence of bacteriophages, such that each dark region of interest indicates an insensitivity or a low sensitivity of the bacterial strain of interest to the viral strain of the bacteriophages.

Step a) may comprise depositing a plurality of droplets, the droplets being spaced apart from one another, two different droplets respectively comprising:

bacteria of various bacterial strains;

and/or various concentrations of bacteria of a given bacterial strain.

Whatever the embodiment, the sample may be divided into various spatial regions that are separated from one another such that:

at least two different spatial regions respectively comprise the same bacterial strain and a different concentration of bacteriophages of a given viral strain;

and/or at least two different spatial regions respectively comprise the same bacterial strain and bacteriophages of various viral strains;

and/or at least two different spatial regions respectively comprise bacteriophages of the same viral strain and various bacterial strains.

The method is then such that each spatial region is associated with one region of interest of each acquired image, two different spatial regions being associated with two different regions of interest, so that analysis of a given acquired image allows information relating to the sensitivity of a bacterial strain to a viral strain of bacteriophages to be obtained in various spatial regions.

The sample may comprise more than ten, or even more than one hundred, different spatial regions that are separate from one another, each spatial region being parameterized by three parameters respectively corresponding to the bacterial strain of interest, to the viral strain of the bacteriophages and to the concentration of the bacteriophages, at least one parameter of two different spatial regions being different.

The sample may be distributed between various fluidic chambers of a fluidic chip, each fluidic chamber corresponding to one spatial region of the sample.

The sample may be formed following a deposition of droplets on the surface of an agar medium, in various positions, the droplets being spaced apart from one another, such that one spatial region is defined by each droplet position. The agar medium may comprise the bacteria and the droplets may comprise bacteriophages. Alternatively, the agar medium may comprise bacteriophages and the droplets may comprise bacteria.

According to one embodiment, the method comprises, prior to step a), an enriching step, comprising:

mixing bacteriophages of given viral strain, or of various viral strains, in an aqueous solution comprising at least one strain of bacteria;

incubating;

filtering the mixture, so as to retain the bacteria and obtain a solution enriched in bacteriophages;

such that, in step a), when the bacteriophages and bacteria are brought into contact the solution enriched in bacteriophages is used.

According to one embodiment, an optical system is interposed between the sample and the image sensor. The optical system defines an image plane and an object. The optical system may be such that:

the image plane is offset with respect to a detection plane, defined by the image sensor, by an image defocus distance;

and/or the object plane is offset with respect to a plane of the sample by an object defocus distance.

The image defocus distance and/or the object defocus distance is preferably smaller than 5 mm, or even than 1 mm, or even smaller than 500 µm. The plane of the sample is a plane lying in the sample. It is preferably the surface of the sample closest to the image sensor. According to this embodiment, in step c), the image is acquired in a defocused configuration.

According to one variant, the optical system allows the image sensor to be conjugated with the sample. The image plane is then coincident with the detection plane formed by the image sensor. The object plane is then coincident with the plane of the sample. According to this embodiment, in step c), the image is acquired in a focused configuration.

The invention will be better understood on reading the description of the exemplary embodiments that are described, in the rest of the description, with reference to the figures listed below.

FIGURES

FIG. 1 shows a device allowing a method according to the invention to be implemented.

FIG. 2A schematically shows a first embodiment of the invention.

Figure 4A:
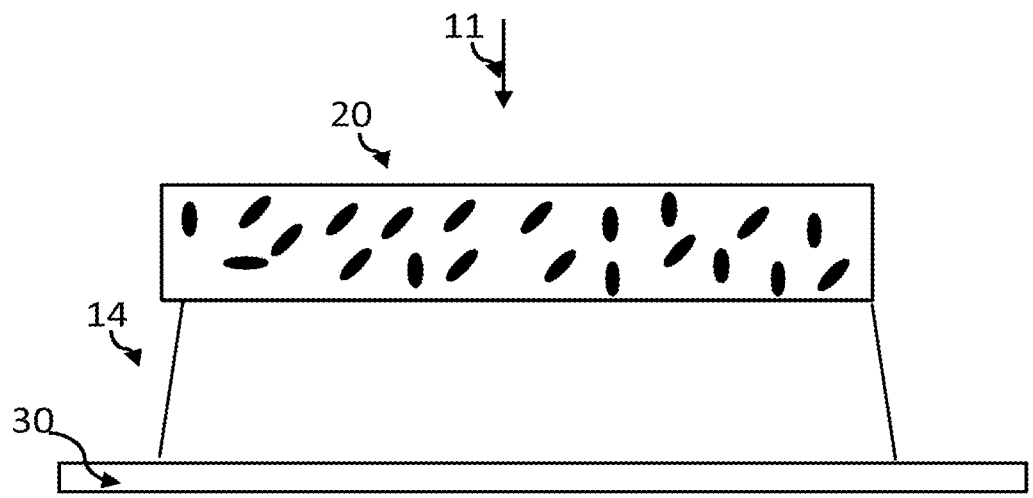
Figure 4B:
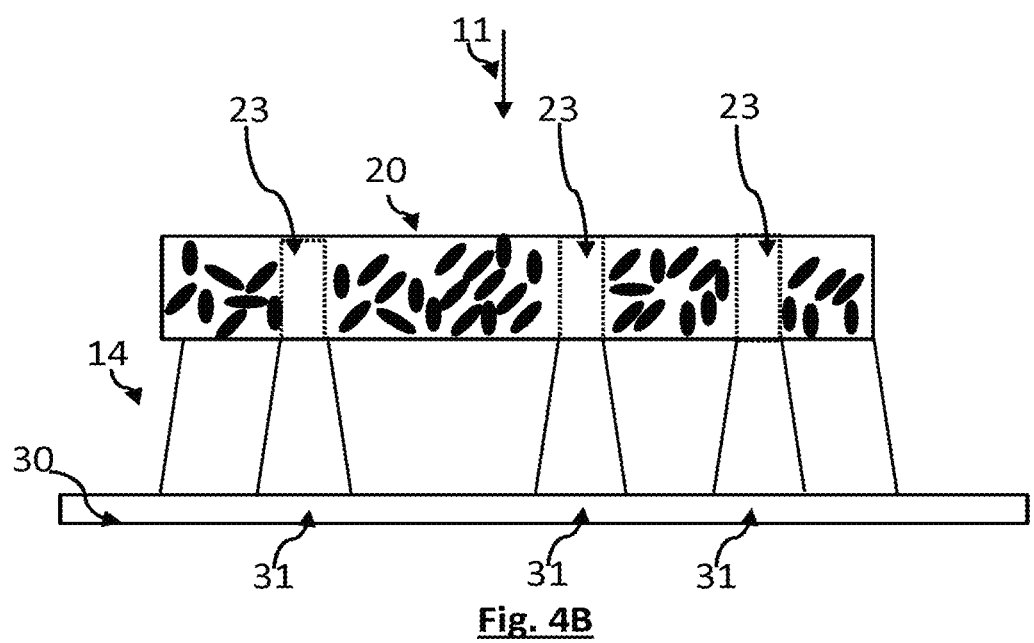

FIGS. 4A and 4B schematically show a second embodiment of the invention.

Figure 4C:
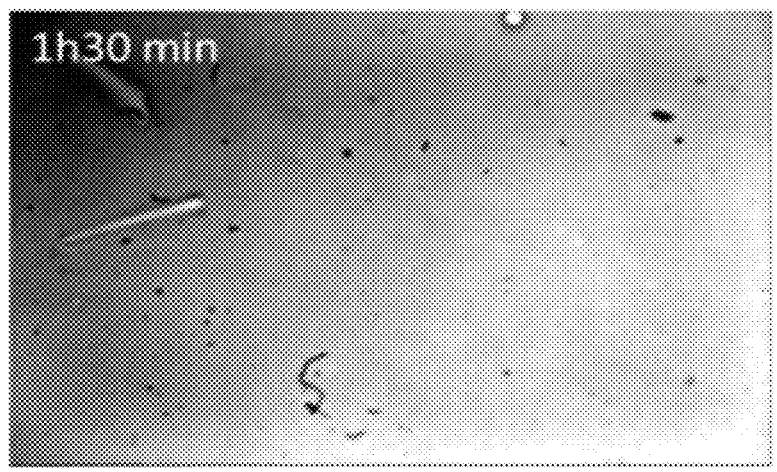
Figure 4D:
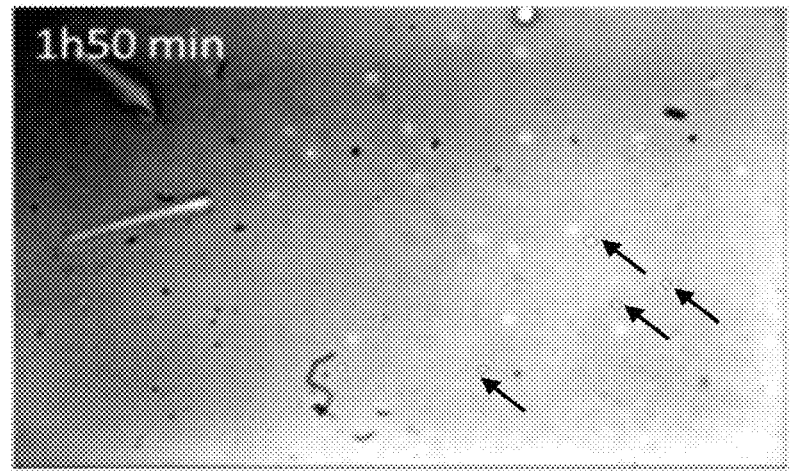
Figure 4E:
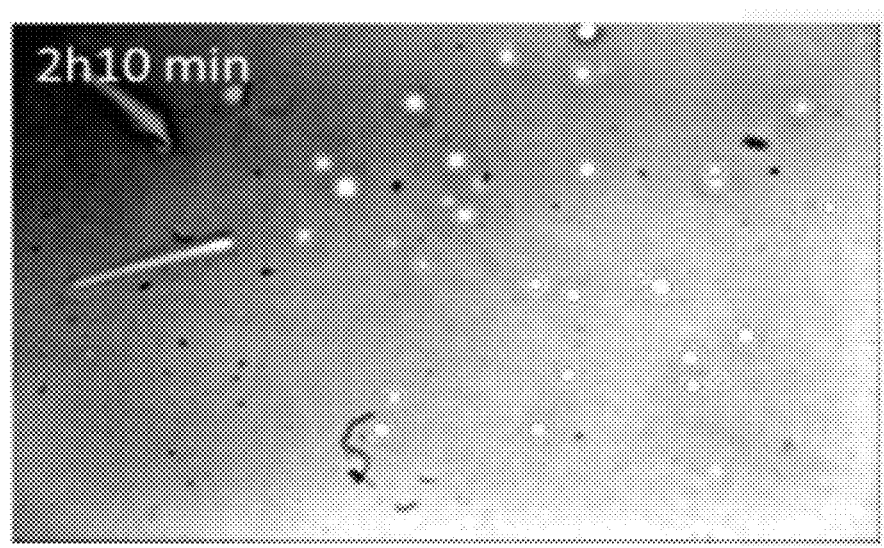

FIGS. 4C, 4D and 4E are images obtained by implementing the second embodiment. They show a formation of viral plaques as a function of time.

Figure 5A:
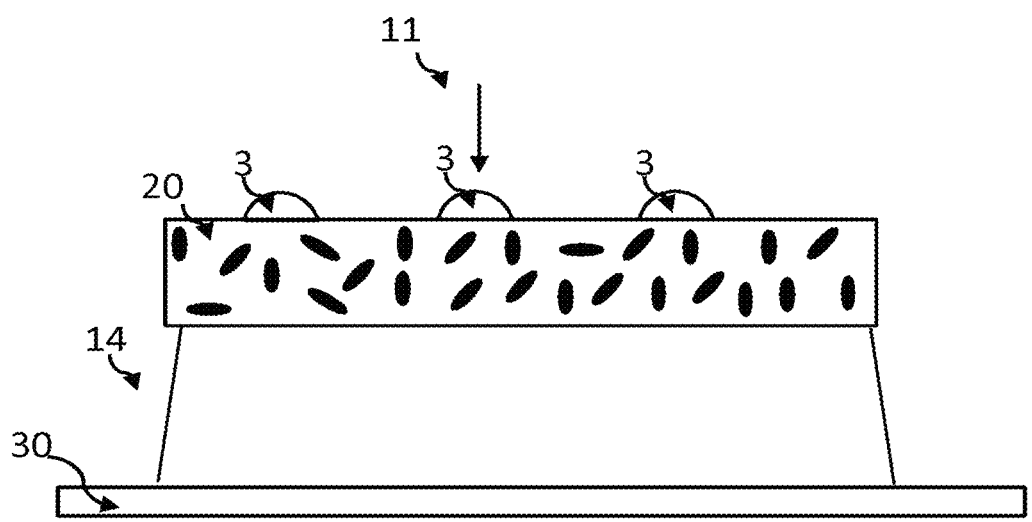
Figure 5B:
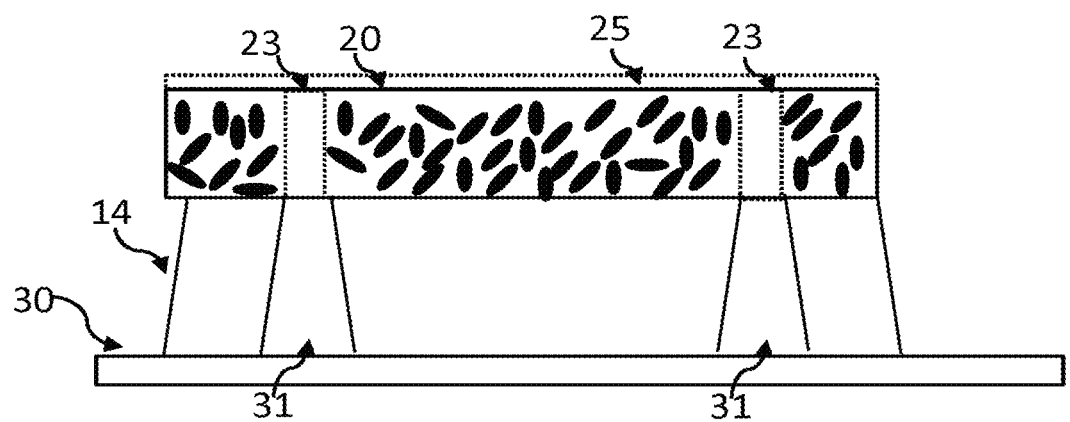

FIGS. 5A and 5B schematically show a third embodiment of the invention.

Figure 5C:
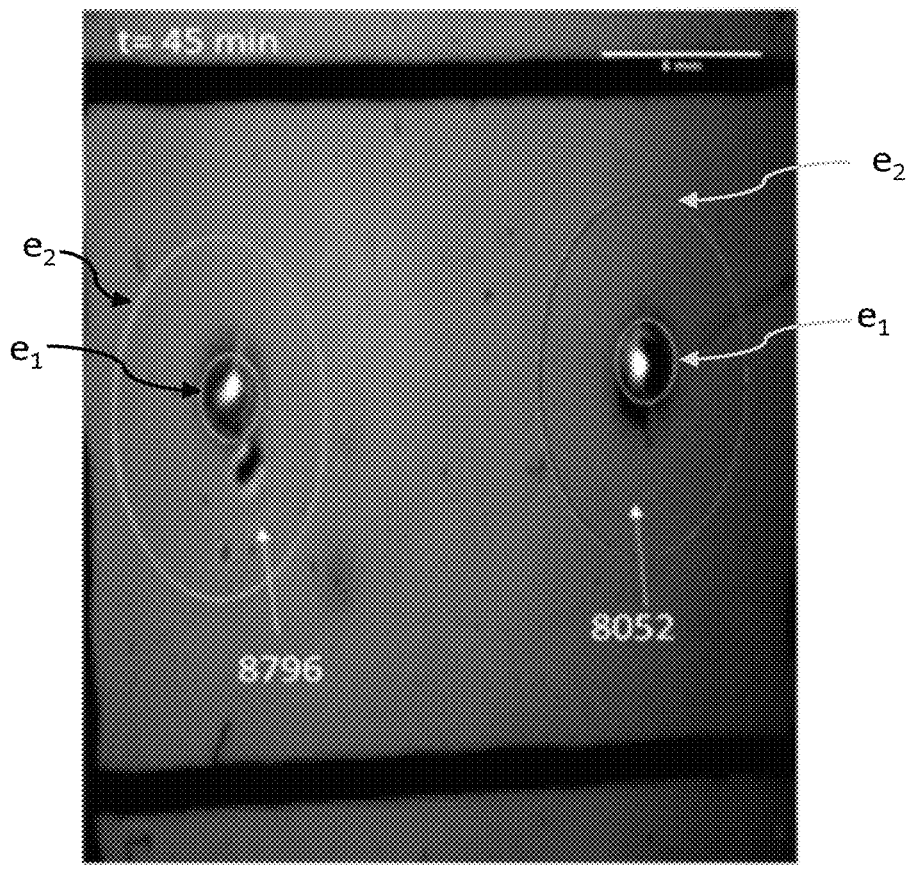
Figure 5D:
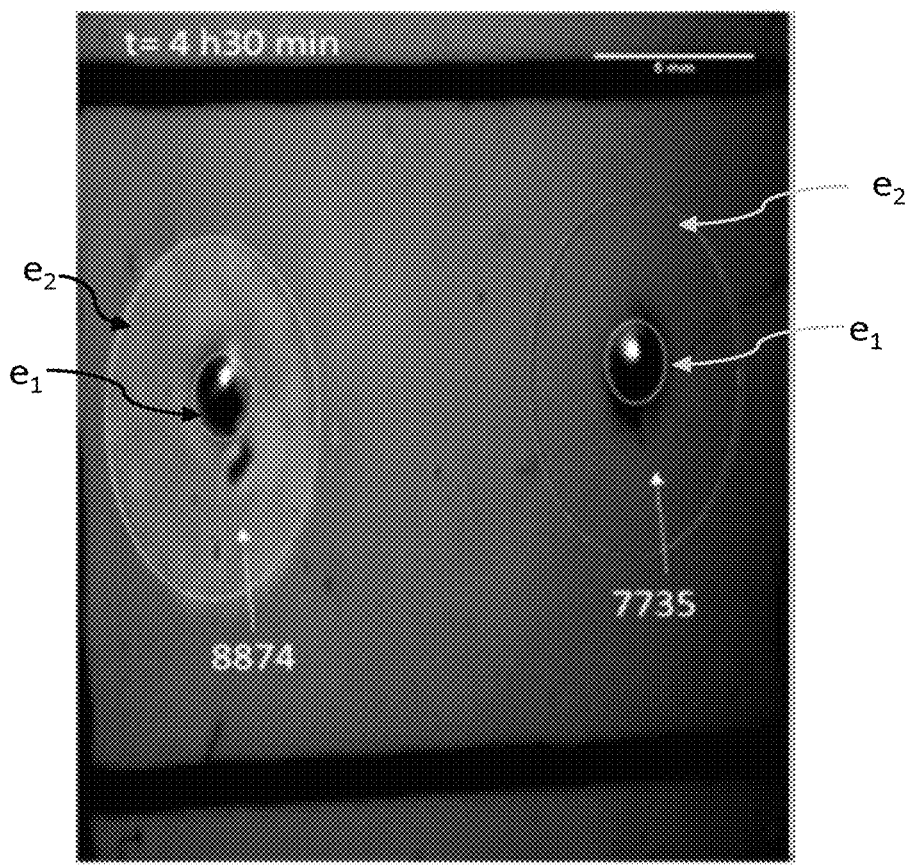

FIGS. 5C and 5D are images obtained by implementing the third embodiment.

Figure 6A:
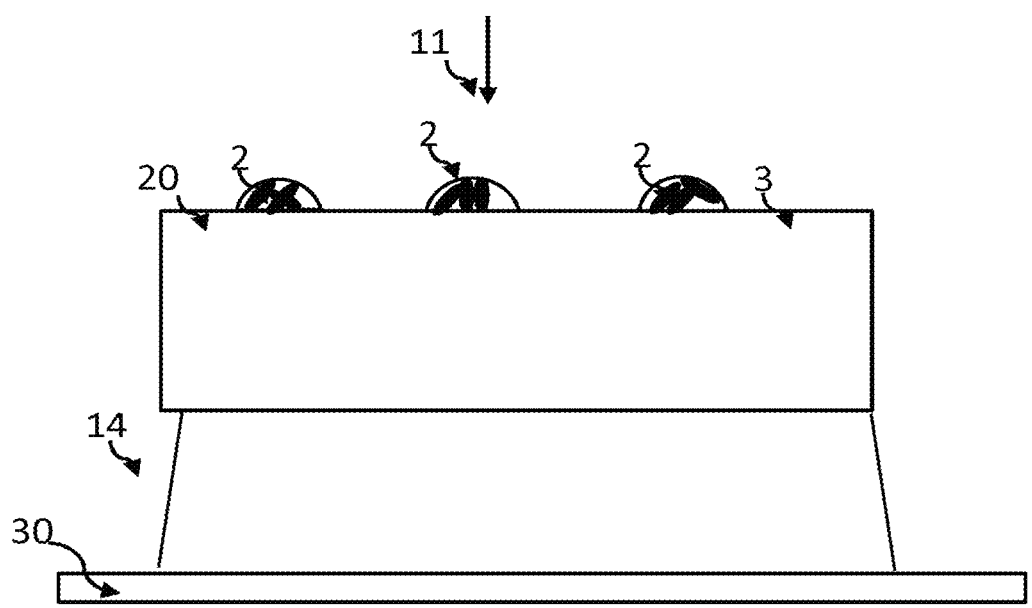
Figure 6B:
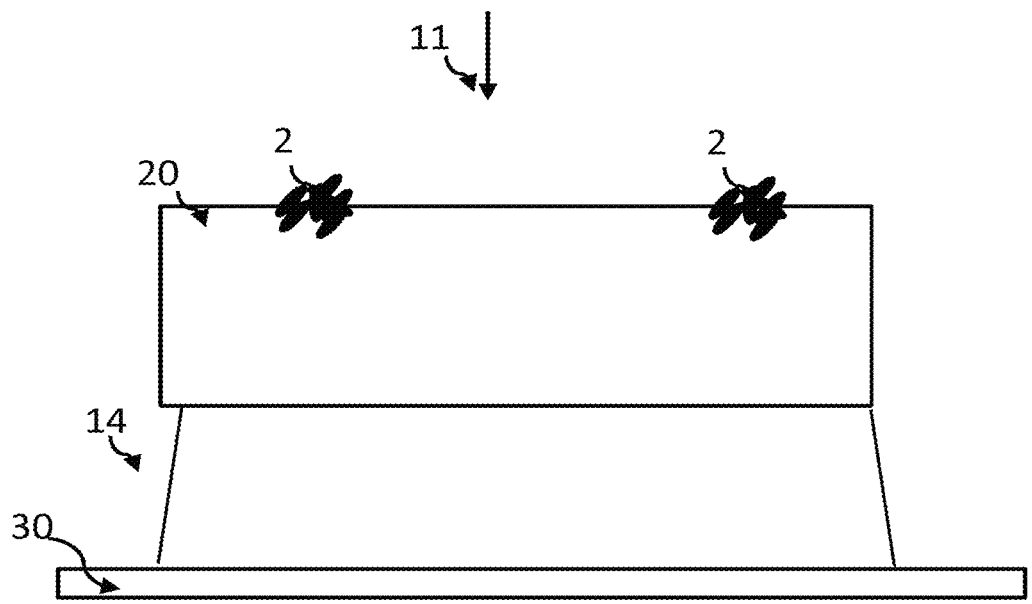

FIGS. 6A and 6B schematically show a fourth embodiment of the invention.

Figure 7:
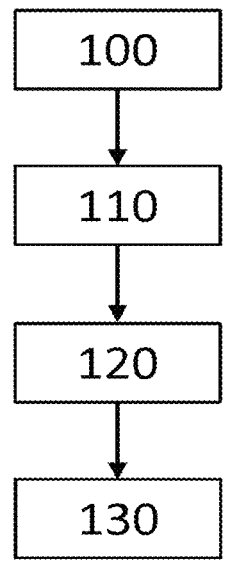

FIG. 7 shows the main steps of implementation of the invention.

Figure 8:
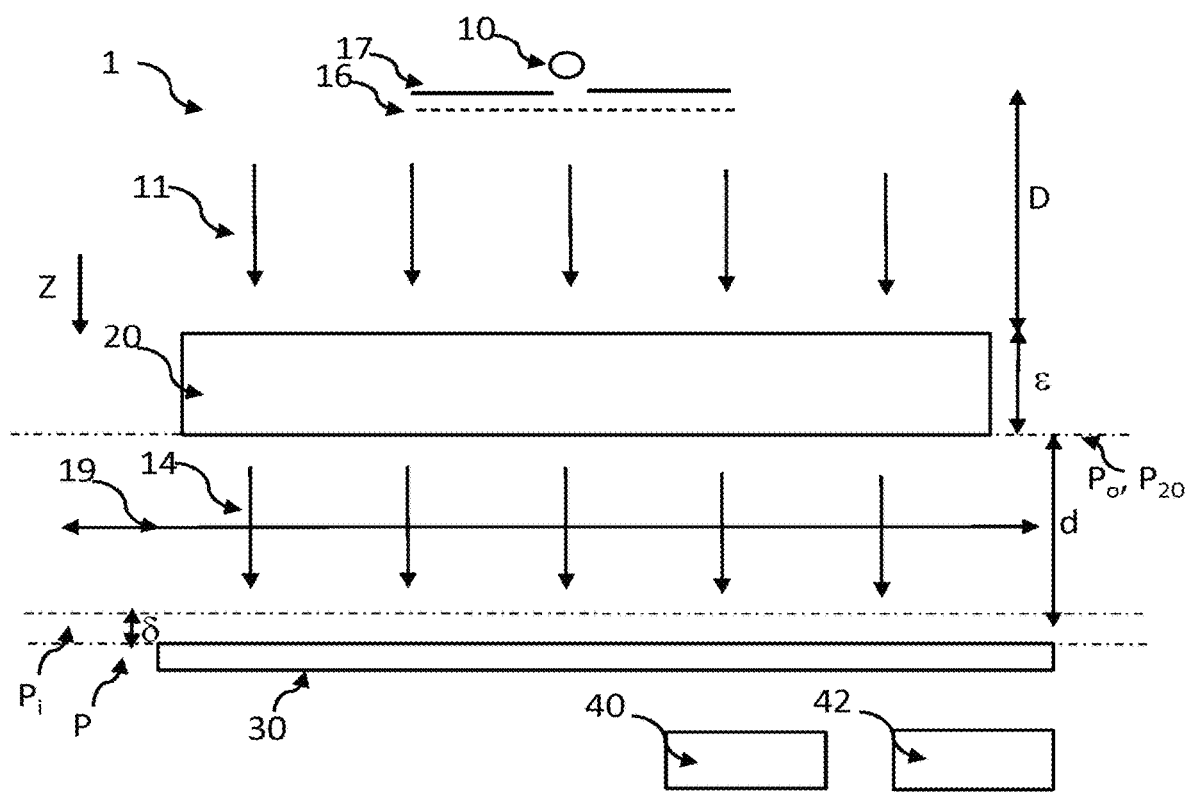

FIG. 8 shows another device allowing the invention to be implemented.

DESCRIPTION OF PARTICULAR EMBODIMENTS

Figure 1:
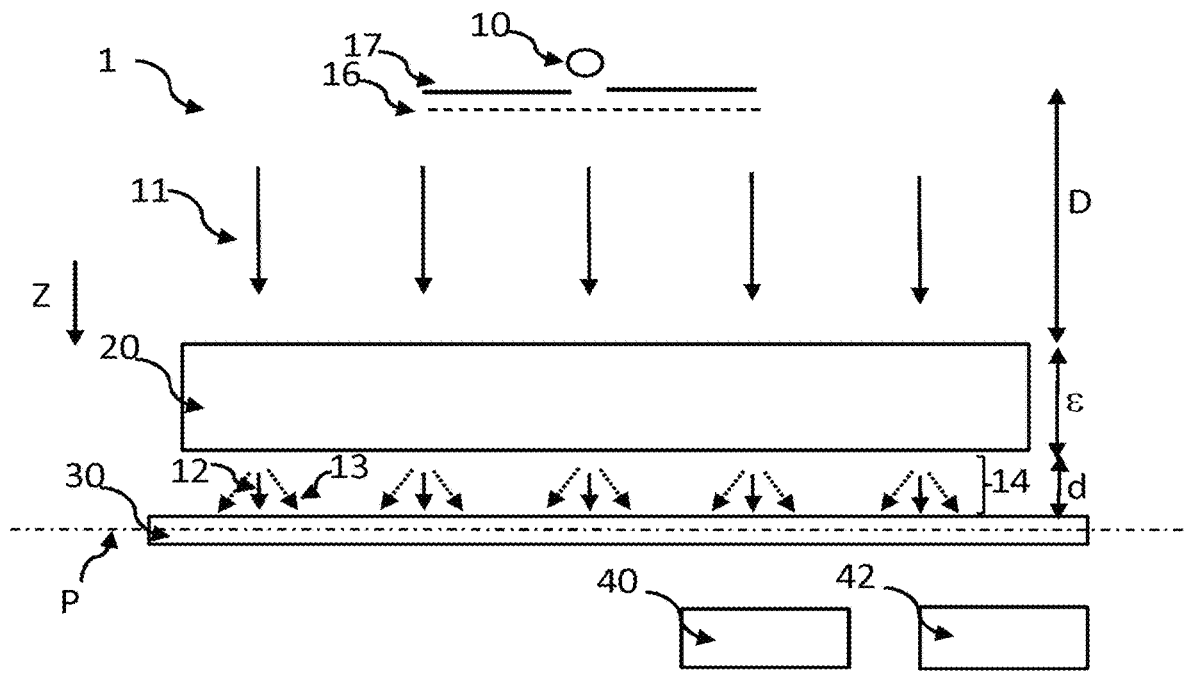

FIG. 1 shows a device allowing the invention to be implemented. A sample 20 is placed between a light source 10 and an image sensor 30. The light source 10 produces an incident light wave 11, the latter propagating up to the sample. Preferably, the incident light wave 11 reaches the sample in the form of a plane wave, or one that may be considered to be plane.

The sample comprises bacteria of one or more bacterial strains, and phages (or bacteriophages), of one or more viral strains. The objective of the invention is to view an optical effect, in the sample, of a lysis induced by the infection of bacteria by certain phages. Preferably, the bacteria are not stained. The invention is based on the observation of the interactions of the bacteria with the incident light wave. More precisely, the presence of bacteria in the sample induces scattering of the incident light wave. The higher the number of bacteria, the more the incident light wave is scattered. The image sensor comprises pixels, which are generally arranged in a matrix array in a detection plane P. The image sensor collects the exposure wave 14 resulting from the interactions of the incident light wave 11 in the sample. The exposure light wave 14, which emerges from the sample, thus consists:

- of a component 12 of the incident light wave that was not absorbed and not scattered by the sample. This component is formed from photons that are usually designated ballistic photons.
- of a component 13 resulting from the scattering of the incident light wave by the sample.

The higher the number of bacteria, the greater the scattered component 13 with respect to the unscattered component 12.

Preferably, the incident light wave 11 lies in an illumination spectral band $\Delta\lambda$ lying in the visible domain. It is preferably comprised between 450 nm and 650 nm, and more preferably between 500 nm and 600 nm. Specifically, it is between 500 nm and 600 nm that the scattering of the incident light wave 11 by the bacteria is maximal. Preferably, the spectral width of the illumination spectral band is narrower than 50 nm, or even narrower than 40 nm. By spectral width, what is meant is the full width at half maximum (FWHM).

The light source 10 is for example a light-emitting diode or a laser diode. It may also be a liquid-crystal display, the advantage thereof being its extensive luminous area, of a few $cm^2$ to a few tens of $cm^2$, producing a uniform illumination. A bandpass filter 16 may be interposed between the light source 10 and the sample 20, so as to adjust the spectral band of the light wave reaching the sample.

The distance D between the light source 10 and the sample 20 is adjusted such that the light source may be considered to be point-like. It may be comprised between 5 cm and 20 or 30 cm. A diaphragm 17, defining an aperture of diameter smaller than 100 μm or 200 μm, may be interposed between the light source 10 and the sample 20. Alternatively, an optical fibre may be interposed between the light source and the sample, so as to form a point light source.

The image sensor 30 may be a CCD or CMOS sensor. Preferably, the detection area is larger than 10 $mm^2$, or even larger than 1 $cm^2$. The inventors have used a sensor the detection area of which is 14.9 mm×22.3 mm, i.e. about 3 $cm^2$. This allows an image of a large field of observation to be obtained. In order to maximize the field of observation, the distance d between the sample 20 and the image sensor 30 is as small as possible. It is preferably smaller than 1 cm. Preferably, the sample 20 is placed in contact with the image sensor, i.e. in contact with a protective cover of the image sensor, or at a few millimetres from the latter. The absence of any magnifying or image-forming optic between the sample 20 and the image sensor 30 will be noted. This does not prevent focusing micro-lenses from being present near the pixels of the image sensor 30. Thus, the image sensor 30 is arranged in a lensless imaging configuration. This allows the field of observation of the image sensor to be maximized. Each image then allows a large volume of sample to be seen. The image sensor may be a monochromic sensor or a colour sensor. It allows an image representative of the exposure wave 14 to be formed.

The image sensor 30 is connected to a processing unit 40, which receives the images acquired by the image sensor. The processing unit 40 is connected to a memory 42 in which instructions for implementing certain image-processing steps described below are stored.

The thickness c of the sample 20 may vary between 100 μm and 1 cm or 2 cm. The configuration of the sample, and its thickness, may vary depending on the embodiments described below. Generally, the sample comprises a medium in which bacteria of at least one bacterial source of interest are brought into contact with phages of a viral strain. The invention is thus used to determine the viral strain and/or the phage concentration allowing the bacteria of the bacterial strain of interest to be lysed.

A first embodiment is presented with reference to FIGS. 2A to 2F. In this first embodiment, the sample comprises a mixture of bacteria and of phages mixed in a solution, preferably an aqueous solution. The aqueous solution contains nutrients, allowing the bacteria to develop. Thus, the aqueous solution comprises a, preferably non-specific, liquid nutrient medium that is conventionally called a "broth". It may for example be a trypticase soy broth, a Columbia agar, or a Luria-Bertani medium.

According to this embodiment, the sample is partitioned into fluidic chambers $22_1$, $22_2$, $22_i$ that are isolated from one another. The index i is an integer designating the rank of a fluidic chip, with $1 \leq i \leq N_i$ where $N_i$ corresponds to the total number of fluidic chambers. The area of each fluidic chamber, parallel to the detection plane P, may for example be comprised between 1 mm² and 10 mm². The fluidic chambers are housed in a fluidic chip 22. Preferably, each fluidic chamber is bounded by an opaque and/or reflective wall $23_1$, $23_2$, $23_i$. This prevents light, scattered inside one fluidic chamber $22_1$, from propagating into another fluidic chamber and forming parasitic light in the latter. Each fluidic chamber $22_i$ contains one elementary sample $20_i$ that may be different from another elementary sample of another fluidic chamber. For a bacterial strain of interest, each elementary sample $20_i$ may thus comprise phages of a given viral strain, with a predefined concentration.

Thus, this embodiment allows the sample to be divided into various spatial regions, each spatial region corresponding to one fluidic chamber $22_i$ containing one elementary sample $20_i$. Each elementary sample may be parameterized by three parameters:
the bacterial strain;
the viral strain;
the concentration of the phages of the viral strain.

Between two different elementary samples, corresponding to two different spatial regions, at least one parameter is different, except in the case of replicas.

The number of fluidic chambers $22_i$ is preferably higher than 10, and more preferably higher than 100. Use of an image sensor of large area, such as described above, allows an image in which a high number of fluidic chambers may be simultaneously seen to be acquired. This avoids, or limits, the need for a mechanism allowing the sample 20 to be moved translationally with respect to the image sensor. It will be understood that this embodiment allows a phagogram to be performed. The fluidic chip 22 thus takes the form of a sheet of wells, allowing a multitude of elementary samples that are different from one another to be analysed simultaneously.

The fluidic chip 22 is for example at least partially made from a transparent and preferably biocompatible plastic material, for example COC (cyclic olefin copolymer) or PMMA (polymethyl methacrylate). It has transparent sidewalls $22t$, which confine each elementary chamber $22_i$. The sidewalls preferably extend perpendicular to a Z-axis along which the light wave 11 emitted by the light source 10 propagates.

Figure 2A:
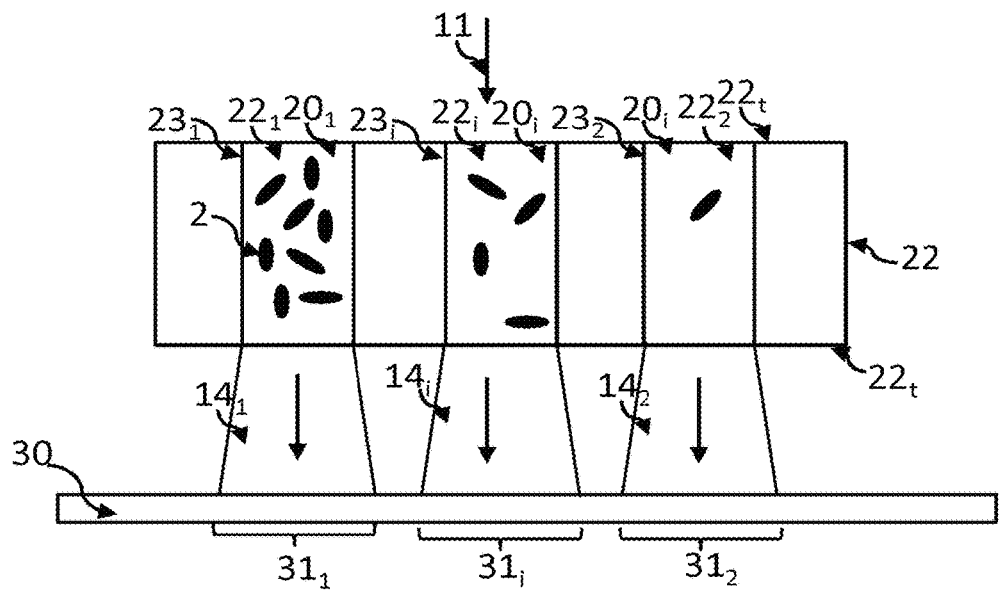
FIGS. 2B and 2C are images obtained by implementing the first embodiment of the invention.
FIG. 2D is a curve obtained experimentally by implementing the first embodiment. It shows a variation in an optical density as a function of time.
FIGS. 2E and 2F illustrate examples of fluidic chips able to be employed.

Each elementary sample comprises an initial number of bacteria 2. In the absence of phages, or in the absence of notable effect of the phages on the bacterial strain, the bacteria proliferate. In FIG. 2A, this case corresponds to the fluidic chamber $22_1$. When the phages are able to infect the bacteria of interest, and to engender their lysis, the number of bacteria of interest decreases, this corresponding to the fluidic chamber $22_2$. The increase or decrease in bacteria leads to a variation in the transport of light through each elementary sample. The images acquired by the image sensor, over time, allow this variation to be assessed and quantified.

The more the number of bacteria increases, the more the light passing through a fluidic chamber is scattered, thereby decreasing the intensity of the exposure light wave 14 propagating toward the image sensor 30. In the example shown in FIG. 2A, the intensity of the light wave $14_2$ is higher than the intensity of the light wave $14_1$. The image sensor comprises pixels 31. Groups of pixels $31_i$ may be defined, each pixel of a given group being exposed to an exposure light wave $14_i$ propagating from one fluidic chamber $22_i$. Thus, each group of pixels $31_i$ is associated with one fluidic chamber $22_i$ and with one elementary sample $20_i$. By acquiring an initial image, or an image of a control sample, then by forming an image at the end of a certain length of time, it is possible to evaluate the variation in the bacterial population of an elementary sample $20_i$, by determining the variation as a function of time in the intensity of the light wave $14_i$ detected by the pixels of a given group of pixels $31_i$. To each group of pixels $31_i$ corresponds one region of interest $ROI_i$ of the image acquired by the image sensor 30. Thus, analysis of each region of interest $ROI_i$ of the image allows the development or inhibition of the development of bacteria in one elementary sample $20_i$ to be viewed. By region of interest, what is meant is portions of the image the intensity of which is considered to be uniform or representative of the sample, or of a portion of the sample.

Figure 2B:
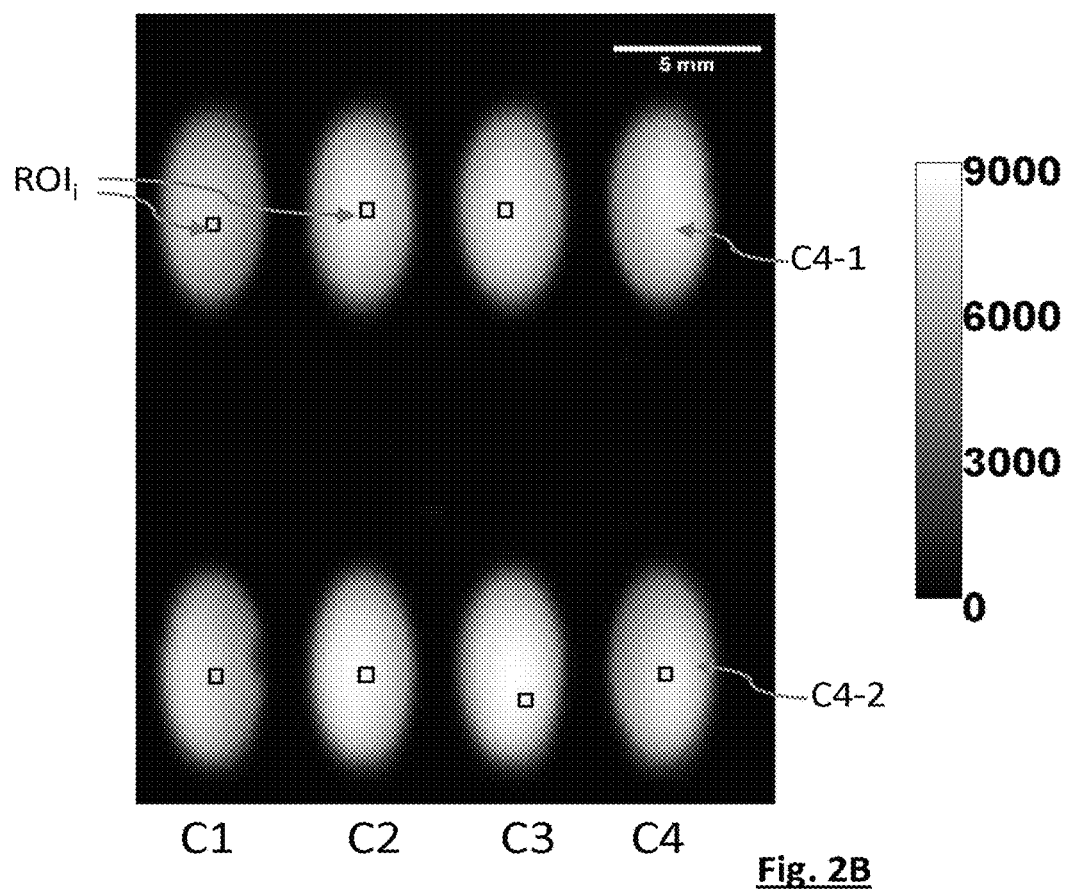
Figure 2C:
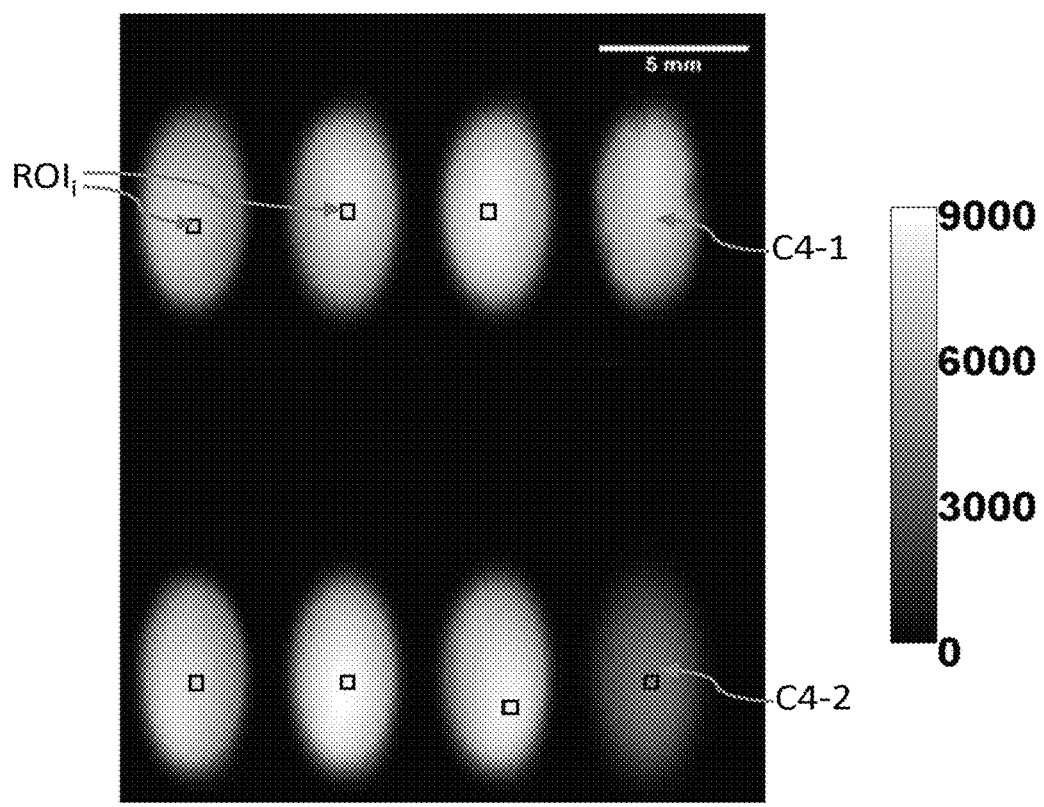

FIGS. 2B and 2C illustrate an example of implementation of the first embodiment. The components and experimental parameters were as follows:
fluidic chip 22: chip machined in an aluminium sheet, comprising eight circular chambers of 3 mm diameter (i.e. a cross section of 7.1 mm²);
volume of each fluidic chamber: 35 µL;
image sensor: 1200D CANON® CMOS RGB sensor in APS-C format (dimensions of 14.9 mm×22.3 mm-18 million pixels);
light source 10: liquid-crystal display (LCD) associated with a bandpass filter (FB 560-10 produced by Thorlabs, Inc.) centred on a wavelength of 560 nm and defining a full width at half maximum of 10 nm;
temperature: 25° C.;
distance between the light source and sample: 1 cm;
thickness of each fluidic chamber: 5 mm.

Each sample was sampled from 9 mL of trypticase soy broth (TSB) nutrient medium, into which 250 µL of a culture solution of *Pseudomonas putida* ATCC12633, and 100 µL of a suspension of *Pseudomonas* virus gh1 phages had been introduced. No phages were added to a control chamber. A reference chamber was filled with the liquid nutrient medium, but with no bacteriophages or bacteria. The suspensions of bacteriophages had a viral load equal to $6 \times 10^9$ pfu/mL, $6 \times 10^8$ pfu/mL and $6 \times 10^7$ pfu/mL, respectively. The unit pfu is a unit known to those skilled in the art meaning plaque-forming unit. The load of each suspension of phages was determined by means of a reference method, using an agar medium. Each chamber was duplicated, with the exception of the control chamber and the reference chamber.

The device was placed in a chamber the temperature of which was thermostatically controlled to 25° C. Images were acquired every 2 minutes over a time of 6 hours and 4 minutes. FIGS. 2B and 2C show images acquired at t=30 minutes (initial image) and t=6 h and 4 minutes, respectively. The initial time t=0 corresponds to the inoculation of the bacteria in the liquid medium. The images were formed taking into account only the green pixels of the sensor. In FIGS. 2B and 2C, various regions of interest $ROI_i$ may be seen, each region of interest corresponding to one elementary sample $20_i$. In this example, the regions of interest of columns C1, C2 and C3 correspond to an identical elementary sample: same bacterial strain—same phage concentration.

In FIGS. 2B and 2C, the wells of columns C1, C2 and C3 correspond to concentrations of $6×10^7$ pfu/mL (i.e. MOI=0.01), $6×10^8$ pfu/mL (i.e. MOI=0.1) and $6×10^9$ pfu/mL (i.e. MOI=1), respectively. MOI is the acronym of "multiplicity of infection", this expression being known to those skilled in the art and designating a ratio between a number of phages (in pfu/mL) and a number of bacteria (in cfu/mL) in each sample. The term cfu means "colony-forming unit" and is conventionally used in microbiology.

The fourth column C4 comprises the reference chamber C4-1 and the control chamber C4-2 not containing any phage.

In the control chamber C4-2, the image is seen to darken. This is due to the proliferation of the bacteria in the absence of phage.

For each column, the brightness (i.e. the greyscale levels) of the acquired images was averaged every 2 minutes. An equivalent optical density DO(t) was then computed, the latter being obtained via the expression:

$$DO(t) = -\log_{10}\frac{I(t)}{I(t=0)} + 0.055$$

where I(t) is the brightness at a measurement time t, which corresponds to an average greyscale level and I(t=0) is the brightness at the initial time t=0. The constant 0.055 was added so that the optical density at the initial time corresponds to that measured by a spectrophotometer.

Figure 2D:
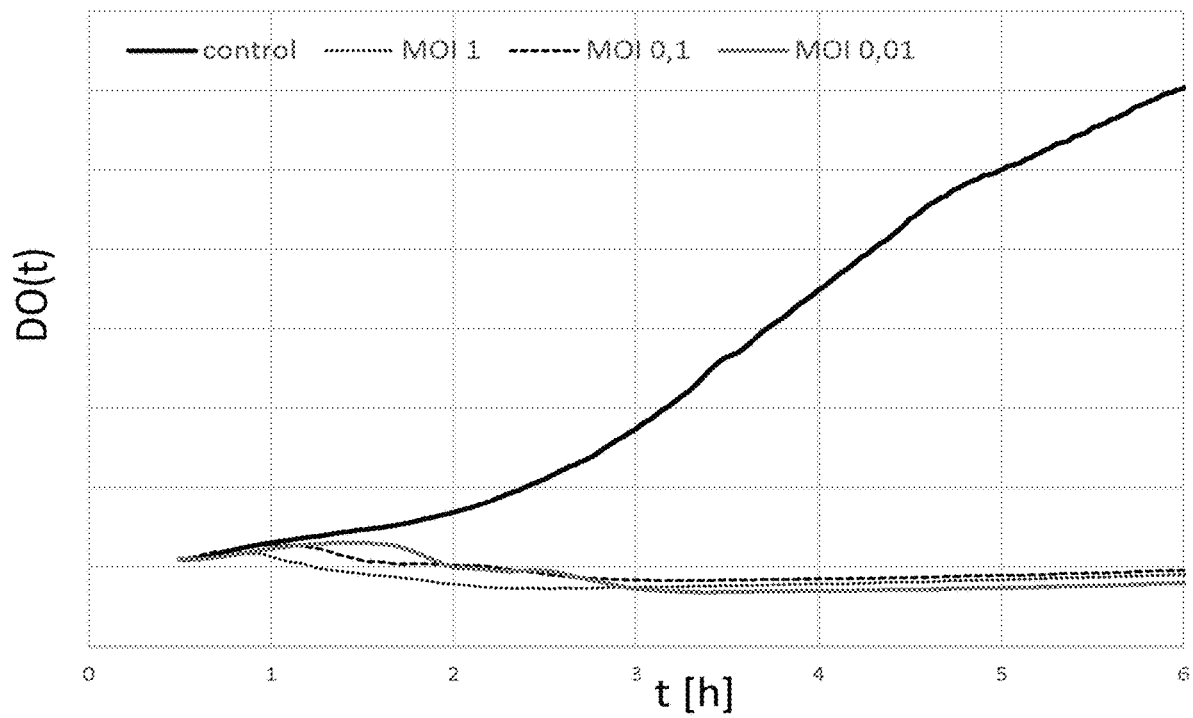

FIG. 2D shows the variation in the equivalent optical density DO(t) (y-axis) as a function of time (x-axis—unit: hours).

From these curves, it may be seen that, under the action of the phage, and for all of the phage concentrations in question, optical density increases for a few hours after the initial time but then stabilizes. In the control chamber, optical density increases continuously. Comparison of the optical densities respectively measured in the control chamber and in the other chambers demonstrates the inhibition of the development of the bacteria by the phage. The action of the phage becomes perceptible two hours after the initial time.

It may be seen that the invention allows the action of a phage on bacteria to be tracked in real time, and for this to be done simultaneously for a plurality of elementary samples $20_i$. It is possible to define, for each sample, a detection threshold that, when crossed, indicates that bacterial proliferation in the sample is suspected. Such a threshold may be defined using the average optical density measured for the control sample, and a dispersion indicator a, the standard deviation for example, at a measurement time or at various measurement times. The detection threshold may be equal to $\mu+k\sigma$, k being a strictly positive real number that is preferably higher than 1 or 2, and for example equal to 5. The establishment of such a detection threshold may easily be automated, and allows the presence of a bacterial proliferation to be recognized early on, for example between 5 h and 10 h. Other thresholds, based on a comparison between the control sample and samples containing phages may be defined.

Figure 2E:
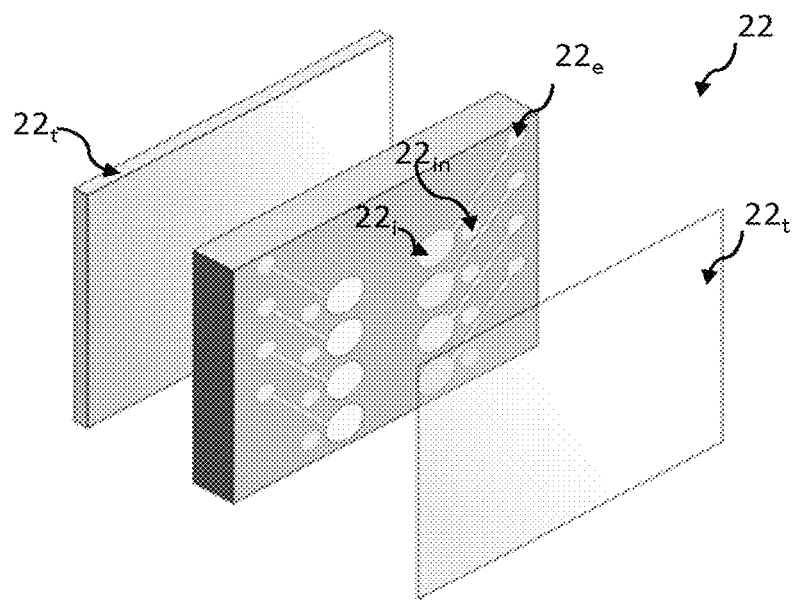

FIG. 2E schematically shows a fluidic chip 22 allowing the invention to be implemented. The fluidic chip comprises fluidic chambers $22_i$, such as described above, respectively closed by two sidewalls $22t$. One sidewall may take the form of a transparent adhesive film. The other sidewall $22t$ may be made using a transparent material that is preferably permeable to oxygen, so as to allow an oxygenation of the fluidic chambers $22_i$, this being necessary for the development of certain bacteria. Thus, it is preferable for at least one sidewall bounding each fluidic chamber to be permeable to oxygen. It may for example be a question of PDMS (polydimethylsiloxane) or TPX (polymethylpentene), the latter being described in document EP0745667.

The nutrient medium and/or the phages may be placed beforehand in each fluidic chamber $22_i$, for example in a freeze-dried state. In the example shown in FIG. 2E, each fluidic chamber $22_i$ is connected, by a fluidic channel, to an inlet $22_{in}$ and vent $22_e$. Each fluidic chamber is filled by syringe, the solution containing the bacteria being introduced via the inlet $22_{in}$. The vent $22_e$ allows air to escape from the fluidic chamber during filling. A filter that blocks liquids but that is permeable to gases may be placed in the vent $22_e$.

Figure 2F:
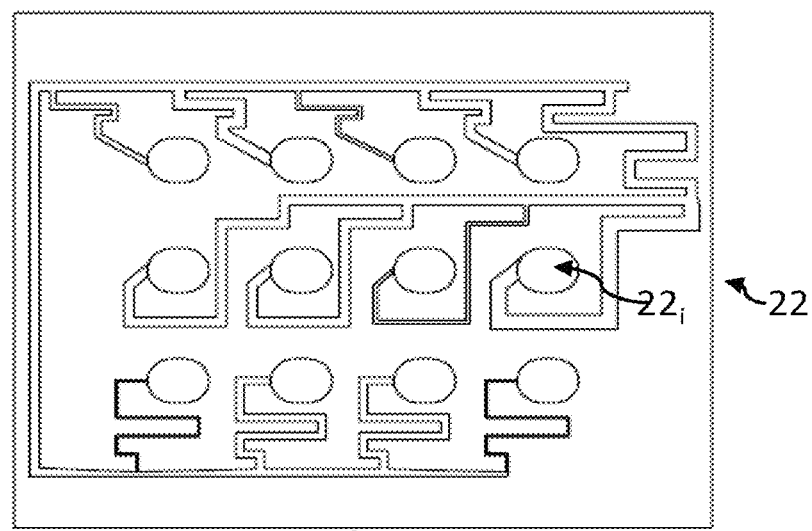

Alternatively, as shown in FIG. 2F, each fluidic chamber is initially under vacuum. Each fluidic chamber is filled via a common inlet. When the fluidic chip 22 is placed under vacuum, the aqueous solution containing the bacteria migrates toward each fluidic chamber. The bacteriophages are placed beforehand in each fluidic chamber, in the freeze-dried state. The bacteria and the bacteriophages are therefore brought into contact during the filling of each fluidic chamber.

According to another possibility, various fluidic chambers respectively contain various bacterial strains. The latter may be present in a freeze-dried state. In this case, each fluidic chamber may be filled via a common inlet, through which a phage-containing solution flows. The objective is then to identify viral strains that may be relevant to certain bacterial strains. According to this possibility, provision may be made for a prior step of phage enrichment. In this step, the various bacterial strains are placed in the same chamber, into which a solution of phages, comprising a single viral strain or a plurality of viral strains, is mixed. If, among the bacterial strains present, a strain is sensitive to a phage, the latter is replicated, this leading to an increase in its concentration. A non-specific amplification of phages is thus obtained. The mixture is then filtered, so as to retain the bacteria, the filtration size possibly being about 0.2 µm. The bacterial strains are then distributed between various fluidic chambers, so as to end up with a single bacterial strain per well. The filtered solution is injected into each fluidic chamber, so as to identify the bacterial strain sensitive to the phage.

This embodiment may be adapted to test the effect of various viral strains on a given bacterial strain. To this end, various fluidic chambers may respectively contain phages of various phage strains. Within a fluidic chamber containing a bacterial strain sensitive to the phage, no bacterial proliferation is observed, and the phage is amplified specifically. When the bacterial strain of a chamber is insensitive to the phage, a bacterial proliferation is observed.

In this embodiment, an optical density or, more generally, a variation in a light intensity transmitted by each elementary sample $20_i$ and detected by the image sensor is measured. In order to obtain a uniform illumination of each elementary sample $20_i$, i.e. of each elementary fluidic chamber $22_i$, it is preferable for the light source 10 to be an area source, for example a liquid-crystal display. This promotes the compactness of the device. Alternatively, a point light source 10 may be used, provided that the sample is placed sufficiently far away therefrom.

Figure 3A:
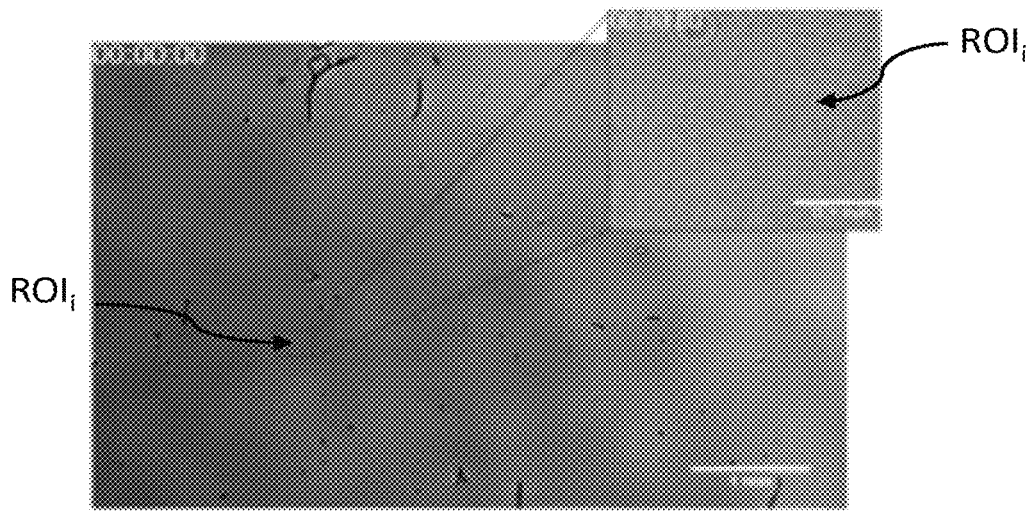
FIGS. 3A and 3B are images obtained by implementing a variant of the first embodiment.
Figure 3B:
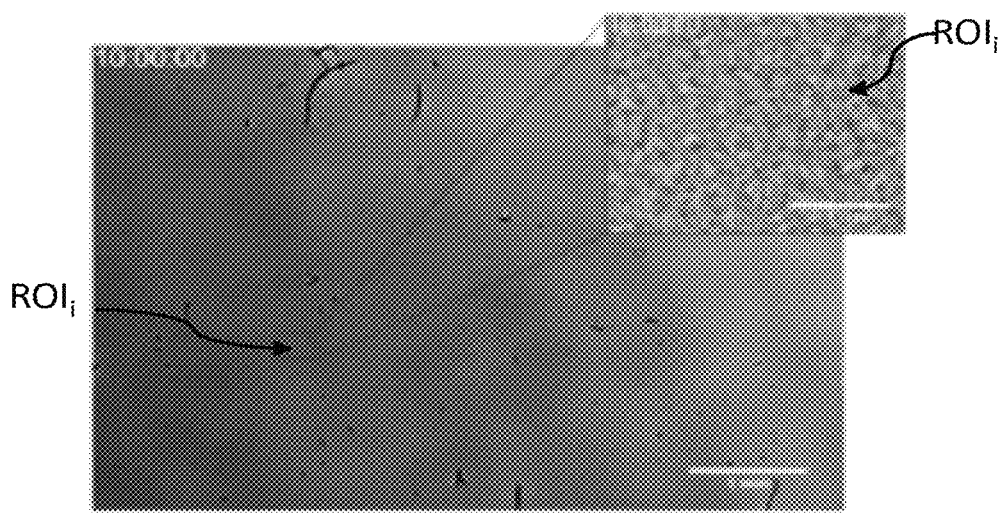

FIGS. 3A and 3B illustrate a variant of the first embodiment, in which each elementary sample is present, in the liquid state, in one fluidic chamber. According to this variant, the presence of microorganisms is quantified via an analysis of the texture of the image. Under the effect of the development of the bacteria, it has been observed that the texture of the images becomes more marked. For each region of interest $ROI_i$ of an acquired image, a texture indicator is established, so as to characterize the elementary sample $20_i$ corresponding to the region of interest. The texture indicator may be a vector, or a scalar quantity. This embodiment is mainly intended for samples of small thickness, for example comprised between 100 μm and 1 mm, and preferably between 100 μm and 250 μm. In FIGS. 3A and 3B, the regions of interest in question have been enlarged.

The texture of the image results from the formation of interference patterns on the image sensor, these patterns resulting from interference between the light wave 12 transmitted by the sample, and the light wave 13 resulting from the scattering of the incident light wave 11 by the sample. According to this embodiment, it is preferable for the light source to be spatially coherent (point-like), and sufficiently far away from the detector for the incident light wave 11 to reach the sample in the form of plane waves, or waves that may be considered as such.

Figure 3C:
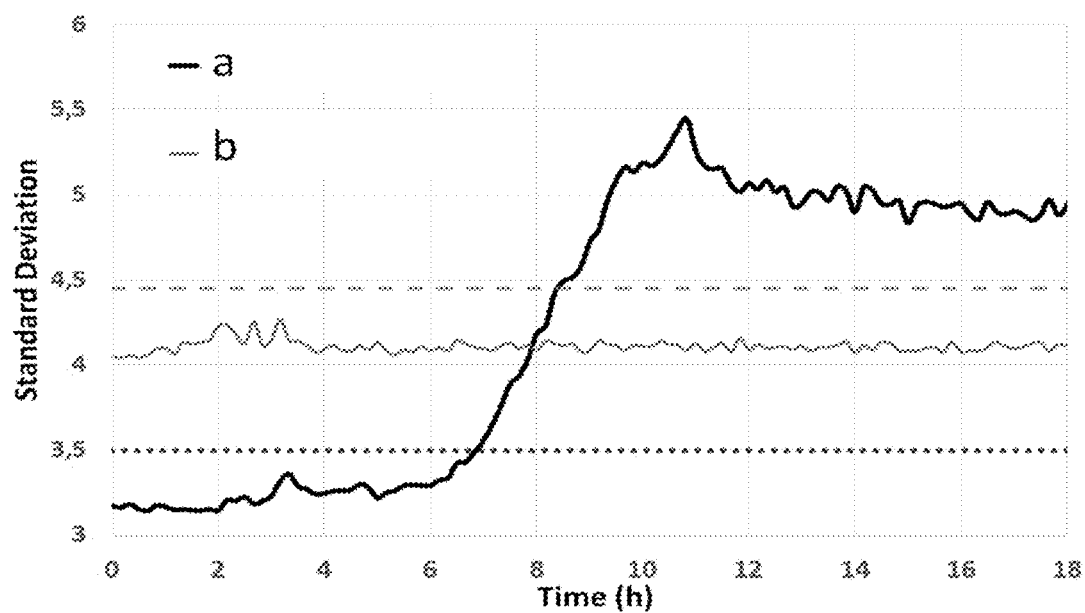
FIG. 3C shows a curve obtained experimentally by implementing the variant of the first embodiment. It shows a variation in a texture indicator as a function of time.

FIGS. 3A to 3C illustrate an example of implementation of the variant of the first embodiment. The components and experimental parameters were:
  fluidic chip 22: microscope slide on which a Geneframe fluidic chamber of 250 μm thickness is deposited, the fluidic chamber being closed by another microscope slide;
  volume of each fluidic chamber: 25 μL;
  image sensor: 10.5 Mpixel monochromic sensor of 1.67 μm side length, forming a detection area of 29.5 mm² (6.4 mm×4.6 mm);
  light source 10: light-emitting diode centred on the wavelength of 650 nm with a full width at half maximum of 40 nm;
  temperature: 30° C.;
  distance between the light source and sample: 5 cm;
  thickness of each fluidic chamber: 250 μm.

In this example, the fluidic chamber is not partitioned. There is only a single analysed sample. The sample was sampled from 9 mL of trypticase soy broth (TSB) nutrient medium, into which 250 μL of a culture solution of *Pseudomonas putida* ATCC12633 diluted by a factor of $10^2$ had been introduced. 100 μL of a suspension of *Pseudomonas* virus gh1 phages, known to infect *Pseudomonas putida* bacteria, and the concentration of which was estimated to be $7 \times 10^5$ pfu/mL, was added. 30 μL of sample was sampled and introduced into the fluidic chip 22.

FIGS. 3A and 3B show an image of the fluidic chamber at an initial time and 10 hours after the initial time, respectively. These images were obtained using a control sample, without any phage. They illustrate the variation of the texture of the image when the bacteria develop. For each image, a texture descriptor was determined by determining a standard deviation of three small regions of 80 pixels×80 pixels of the image. In FIGS. 3A and 3B, such a small region has been shown. The texture descriptor corresponds to an average of the three standard deviations thus determined. FIG. 3C shows a variation in the determined texture indicator:
  for a control sample, without any phage (curve a)
  for a sample containing $7 \times 10^5$ pfu/mL of *Pseudomonas* virus gh1 phages (curve b).

This figure was obtained by acquiring images every 10 minutes for a duration of 18 hours. It may be seen that:
  for the control sample, the texture descriptor increases, under the effect of the bacterial proliferation;
  for the sample comprising the phages, the texture descriptor stagnates over time, indicating an inhibition of the development of the bacteria.

It is possible to define a detection threshold that, when crossed, indicates that bacterial proliferation in the sample is suspected. Such a threshold is determined using a mean (or median) value p and a dispersion indicator, the standard deviation a for example, of the texture descriptor in a short time period, for example 1 h or 2 h, after the initial time. The detection threshold may be equal to $\mu + k\sigma$, k being a strictly positive real number that is preferably higher than 1 or 2, and for example equal to 5. The establishment of such a detection threshold may easily be automated, and allows the presence of a bacterial proliferation to be recognized early on, for example between 5 h and 10 h.

FIGS. 4A to 4E illustrate a second embodiment, in which the bacteria and phages are located in an agar medium containing a nutrient medium. The nutrient medium is transparent and is preferably non-specific. The agar medium contains phages, in the virion state. The latter infect the bacteria and multiply following the lysis of the latter. The lysis of bacteria thus propagates locally, in the vicinity of the locations of the virions in the initial state. The propagation allows a viral plaque, corresponding to a portion of the agar medium depleted in bacteria, to be formed. Thus, level with the viral plaques, the transmission of light is increased with respect to the other portions of the sample, in which portions the bacteria proliferate.

Such an agar medium may be made up by mixing a conventional agar nutrient medium that is brought above its gelling point, for example between 40° C. and 60° C., with an aqueous solution comprising bacteria and phages. Thus, the sample comprises a soft agar medium, comprising bacteria and phages. The thickness of the sample may be comprised between 2 mm and 5 mm. Placing the bacteria and phages at such a depth allows the lysis of the bacteria to be better observed. The agar-agar mass fraction is for example comprised between 0.5% and 1.4%, such an agar medium conventionally being denoted by the term "soft agar".

According to one variant, one portion of the thickness of the sample is formed from a standard nutrient medium, without any bacteria or phage. It may for example comprise agar-agar in a mass fraction of 1.5%. The function of this nutrient medium is to form a reservoir of nutrients for the bacteria. However, because the method for analysing a sample is fast, taking about a few hours or a few tens of hours, the presence of such a reservoir of nutrients is not necessary. The absence of such a reservoir is considered to be advantageous, because it prevents the latter from scattering the light.

FIGS. 4A to 4B schematically show a sample 20 at an initial time, considered to correspond to the formation of the superficial layer $20s$, and at a time subsequent to the initial time, respectively. In the vicinity of the phages initially present, bacteria are lysed, and the lysis of the bacteria gradually propagates under the effect of the replication of the phages. Depleted regions 23, or viral plaques, form in the superficial layer 20s of the sample. The transmission of the light through the viral plaques is higher than through the rest of the sample. Thus, when the sample is illuminated by a light source, groups of pixels 31 located facing the depleted regions 23 collect a higher amount of light than the amount of light captured by the other pixels. In the image acquired by the image sensor, this results in the appearance of light regions of interest. Each light region of interest corresponds to one viral plaque. Counting the light regions of interest allows a viral load of the solution comprising the bacteriophages to be estimated. This viral load may be expressed as a number of plaque-forming units (pfu).

FIGS. 4C, 4D and 4E are experimental images acquired 1h30, 1h50 and 2h10 after the preparation of a sample, respectively. The following were mixed in 5 ml of soft agar (50% TSA (trypticase soy agar)-50% TSB (trypticase soy broth)): 250 µl of a culture of *Pseudomonas putida* ATCC12633 bacteria (about $10^9$ cfu/mL) in a broth, and 100 µl of an aqueous solution comprising *Pseudomonas* virus gh1 phages. The preparation was homogenized by vortexing. 2 mL of the preparation was poured into a Petri dish of 3.5 mm diameter, forming a fluidic chamber. The sample was placed on a 30 Mpixel image sensor and these were placed together in a chamber the temperature of which was thermostatically controlled to 30° C. The experimental parameters were the following:

image sensor: 1200D CANON® CMOS RGB sensor with dimensions of 14.9 mm×22.3 mm-18 million pixels;

light source 10: light-emitting diode centred on the wavelength of 560 nm;

distance between the light source and sample: about 20 cm;

thickness of each fluidic chamber: 2 mm.

The initial time t=0 is considered to be able to be set equal to the time of deposition of the preparation in the Petri dish. The biomass is considered to be uniformly distributed in the dish. Over time, viral plaques form, these corresponding to light spots in the images 4C, 4D and 4E. In FIG. 4D, certain light spots are indicated by arrows. These images were formed using the green pixels of the image sensor. The gradual formation of light regions of interest in the images may be seen.

According to another approach, a partitioned fluidic chip, such as described with respect to the first embodiment, is used. The fluidic chip comprises fluidic chambers $22_i$ that are separated from one another. Each fluidic chamber contains a mixture of phages and a freeze-dried cold gelling agent. Each fluidic chamber may be fed with a solution comprising bacteria. An agar medium, comprising a mixture of bacteria and phages, then forms. The cold gelling agent is hydrosoluble. It is configured to gel when it makes contact with an aqueous solution at room temperature, then forming a hydrogel. It may be a hydrosoluble polysaccharide. The cold gelling agent may be chosen from carboxymethyl cellulose, guar gum, gum arabic, gellan gum, xanthan gum, or a gelling agent obtained from animal bones, for example from pig, cow or chicken bones.

Such an approach allows the sample to be divided into various spatial regions, each spatial region corresponding to one fluidic chamber.

Alternatively, the fluidic chip is brought, after it has been filled, to a gelling point of the agar medium containing the bacteria. Thus, the agar medium comprising the bacteria is able to fill each fluidic chamber, so as to mix, in each chamber, with the phages provided beforehand in the freeze-dried state. This avoids using a cold gelling agent, the latter possibly causing scattering.

A third embodiment is shown in FIGS. 5A to 5D. According to this embodiment, the bacteria are initially present in an agar medium, or in a superficial layer of a solidified agar medium. Droplets of a solution comprising phages 3 are deposited on the surface of the latter. The droplets are separate from one another. When the bacteria contained in the agar medium are sensitive to the bacteriophage, viral plaques form in the sample, as described with respect to the second embodiment. One advantage of this embodiment is that the position of each deposited droplet may be known, this allowing the development of viral plaques facing each of these positions to be researched. This facilitates the image-processing step.

FIGS. 5A and 5B schematically show this embodiment, during the deposition of the droplets on the agar medium, and following the formation of viral plaques when the bacteria are sensitive to the viral strain of the phages present in the droplets, respectively. The deposited droplets may respectively comprise various viral strains, and/or various concentrations of phages of a given viral strain. Just like the first embodiment, this embodiment allows tests of various phages or of various concentrations to be carried out in parallel. A formation of two viral plaques has been schematically shown in FIG. 5B. Just as in the second embodiment, under the effect of the lysis of the bacteria, viral plaques appear, through which the transmission of light is higher than in the rest of the sample. The pixels 31 located facing the viral plaques collect a signal the amplitude of which is higher. As a result, light spots appear in the image formed by the image sensor.

A sample was prepared by mixing 120 µL of a culture medium containing *Pseudomonas putida* ATCC12633, and 6 mL of soft agar-agar (7.5 g/L agar-agar). This preparation was poured into a Petri dish, this allowing an agar medium of about 2 mm thickness to be obtained. Droplets of 5 µL were then deposited on the surface, these droplets comprising:

either a suspension of *Pseudomonas* virus gh1 phages the load of which was estimated to be $3.6 \times 10^6$ pfu/mL;

or a pharmaceutical diluent to simulate the presence of a phage that is inactive with respect to the bacterial strain used.

The droplets were dried (15 minutes), then the sample was deposited in a chamber the temperature of which was thermostatically controlled to 28° C. The experimental parameters were as follows:

image sensor: 1200D CANON® CMOS RGB sensor with dimensions of 14.9 mm×22.3 mm-18 million pixels;

light source 10: light-emitting diode centred on the wavelength of 560 nm;

distance between the light source and sample: about 20 cm;

thickness of the fluidic chamber: 2 mm.

A small thickness (between 0.1 mm and 1 mm) of oil 25 may be placed on the sample, so as to avoid drying. The oil 25 may be silicone oil, allowing oxygen to diffuse up to the nutrient medium.

FIGS. 5C and 5D are experimental images acquired 45 minutes and 4 h30 after the deposition of droplets on a sample, respectively. In each of these figures, each ellipse e1 shows the region of deposition of the droplet and each ellipse e2 corresponds to a zone of analysis of the image. In each of these images, the ellipses e1 shown on the left and on the right correspond to the deposition of the phage and of the solution of pharmaceutical diluent, respectively. By comparing FIGS. 5C and 5D, an increase in the greyscale level in the ellipse e2 on the left of the image may be seen. This corresponds to the formation of a viral plaque. In contrast, in the ellipse e2 located on the right of the image, the greyscale level decreases, following the development of the bacteria.

Such an embodiment allows the sample to be divided into various spatial regions, each spatial region corresponding to a position in which a droplet was deposited. The image acquired by the image sensor allows a plurality of spatial regions to be analysed simultaneously.

A fourth embodiment is schematically shown in FIGS. 6A and 6B. According to this embodiment, an agar medium comprising phages 3 is provided. Droplets of a solution comprising bacteria are deposited on the surface of the latter. The droplets are separate from one another. When the bacteria are not sensitive to the viral strain, they develop on the surface of the sample, forming colonies. When the bacteria contained in the droplets are sensitive to the viral strain of the bacteriophages present in the agar medium, formation of colonies on the surface of the sample is not observed. One advantage of this embodiment is that the position and composition of each deposited droplet may be known, this allowing the development of colonies in each of these positions to be researched. This facilitates the image-processing step.

FIGS. 6A and 6B schematically show this embodiment, during the deposition of the droplets on the agar medium, and following the formation of colonies when the bacteria present in a droplet are hardly or not sensitive to the phage present in the agar medium, respectively. The deposited droplets may respectively comprise various strains of bacteria, or various concentrations of a given strain. This embodiment allows tests of various bacterial strains or of various concentrations of a given bacterial strain to be carried out in parallel. A formation of two colonies has been schematically shown in FIG. 6B. The pixels 31 located facing the colonies collect a signal the amplitude of which is lower. As a result, dark spots appear in the image formed by the image sensor.

Such an embodiment allows the sample to be divided into various spatial regions, each spatial region corresponding to a location in which a droplet was deposited. The image acquired by the image sensor allows a plurality of spatial regions to be analysed simultaneously.

FIG. 7 schematically shows the main steps of a method according to the preceding embodiments.

Step 100: bringing bacterial strains into contact with phages. This step may be carried out in a single fluidic chamber (cf. second, third, or fourth embodiments), or in various fluidic chambers (cf. first embodiment). In this step, the sample may be divided into various spatial regions. These spatial regions may correspond:
  to fluidic chambers that are different from one another (cf. first embodiment);
  or to different positions in which droplets of an aqueous solution of phages are deposited on an agar medium comprising bacteria (third embodiment);
  or to different positions in which droplets of an aqueous solution of bacteria are deposited on an agar medium comprising phages (fourth embodiment).

Step 110: illuminating the sample using the light source;
Step 120: acquiring an image with the image sensor;
Step 130: analysing the image with the processing unit, so as to evaluate a sensitivity of at least one bacterial strain to a least one viral strain.

The advantages of the method such as described previously are:
  detection early on of the lysis of bacteria by phages. Specifically, when using prior-art methods, it is considered to take at least one day to obtain exploitable results;
  an implementational possibility which makes it possible to simultaneously monitor various bacterial strains in combination with various phage strains, or various ratios between the quantities of phage strains and the quantity of strains of bacteria;
  implementational simplicity, without requiring costly hardware.

FIG. 8 shows another device allowing the invention to be implemented. The device comprises an optical system 19 placed between the sample 20 and the image sensor 30. The optical system may be a lens or an objective. The image sensor defines a detection plane P. The sample defines a sample plane $P_{20}$. The plane of the sample is a plane that is preferably parallel to the detection plane and that lies in the sample. It is preferably the surface of the sample closest to the image sensor. The optical system defines an image plane $P_i$ and an object plane $P_o$. In a defocused configuration:
  the image plane is offset with respect to the detection plane by an image defocus distance;
  and/or the object plane is offset with respect to the plane of the sample by an object defocus distance.

The image defocus distance and/or the object defocus distance is preferably smaller than 1 mm, or even smaller than 500 µm.

According to one variant, the optical system allows the image sensor to be conjugated with the sample. The image plane is then coincident with the detection plane formed by the image sensor. The object plane is then coincident with the plane of the sample. According to this embodiment, the image is acquired in a focused configuration.

FIG. 8 shows a defocused configuration in which the object plane $P_o$ is coincident with the plane $P_{20}$ of the sample. The image plane is offset with respect to the detection plane by an image defocus distance δ. Generally, the defocused configuration is preferred when it is sought to quantify a texture of the image.

With respect to the configurations described with reference to FIG. 8, the lensless configuration, illustrated in FIG. 1, is preferred because it allows a compact and inexpensive device to be used.

The invention claimed is:

1. A method for determining sensitivity of a bacterial strain to a viral strain of bacteriophages, the method comprising:
  a) preparing a sample, comprising bringing bacteria of the bacterial strain into contact with bacteriophages, wherein each bacteriophage belongs to the same viral strain, and wherein the bacteria are in a first liquid medium or in a first agar medium;
  b) placing the sample between a light source and an image sensor, wherein the light source emits a light wave in an emission spectral band of from 500 nm to 600 nm;
  c) illuminating the sample using the light source and acquiring images of the sample with the image sensor, in the emission spectral band;
  d) based on each acquired image, determining a sensitivity of the bacterial strain to the viral strain of the bacteriophages, wherein:
  c) comprises acquiring at least two images at successive measurement times;

d) comprises determining a light intensity detected by all or a part of the image sensor in each image respectively acquired at each measurement time, wherein the bacterial strain is:

hardly or not sensitive to the viral strain of the bacteriophages when the detected light intensity decreases between two successive measurement times; or sensitive to the viral strain of the bacteriophages when the detected light intensity does not decrease or increases between two successive measurement times;

wherein none of the bacteria strains and the bacteriophage strains is stained;

the image sensor comprises pixels and focusing microlenses, facing the pixels;

the image sensor comprises a protective cover; and no image forming optic is placed between the sample and the protective cover.

2. The method according to claim 1, wherein a width of the emission spectral band is less than 50 nm.

3. The method according to claim 1, wherein a distance between the sample and the image sensor is less than 5 cm.

4. The method according to claim 1, wherein d) comprises determining an attenuation of a light, emitted by the light source, by the sample, wherein the bacterial strain is:

hardly or not sensitive to the viral strain of the bacteriophages when the attenuation increases between two successive measurement times; or sensitive to the viral strain of the bacteriophages when the attenuation does not increase between two successive measurement times.

5. The method according to claim 1, wherein:

in a), the bacteria and the bacteriophages are mixed in the first liquid medium, wherein the first liquid medium is an aqueous solution;

d) further comprises determining a texture descriptor for each acquired image, wherein the bacterial strain is:

hardly or not sensitive to the viral strain of the bacteriophages when the variation in a texture descriptor is indicative of an increase in scattering of the light by the sample between two successive measurement times; or sensitive to the viral strain of the bacteriophages when the variation in the texture descriptor is indicative of a decrease or a stagnation in scattering of the light by the sample between two successive measurement times.

6. The method according to claim 1, wherein:

in a), the bacteria and the bacteriophages are mixed in the first agar medium;

d) further comprises analysing each acquired image and identifying light regions of interest, wherein each light region of interest corresponds to an infection of bacteria by bacteriophages forming a viral plaque, and wherein each light region of interest indicates a sensitivity of the bacterial strain to the viral strain of the bacteriophages.

7. The method according to claim 6, further comprising:

counting the number of light regions of interest in at least one acquired image; and estimating a viral load of the bacteriophages in the sample based on the number of light regions of interest counted.

8. The method according to claim 1, wherein:

in a), the bacteria are located in the first agar medium, and the bacteriophages are located in a second solution, wherein a) further comprises depositing at least one droplet of the second solution on the first agar medium;

d) further comprises analysing each acquired image and identifying light regions of interest, wherein each light region of interest corresponds to an infection of bacteria by bacteriophages forming a viral plaque, and wherein an appearance of each light region of interest indicates a sensitivity of the bacterial strain to the viral strain of the bacteriophages.

9. The method according to claim 8, wherein a) comprises depositing a plurality of droplets spaced apart from one another, wherein at least two different droplets comprise:

bacteriophages of various viral strains; and/or various concentrations of bacteriophages of the same viral strain; or a combination thereof.

10. The method according to claim 1, wherein:

in a), the bacteriophages are located in a second agar medium, and the bacteria are located in the first liquid medium, wherein a) further comprises depositing a droplet of the first liquid medium on the second agar medium;

d) further comprises analysing each acquired image and identifying:

light regions of interest, wherein each light region of interest corresponds to an infection of bacteria by bacteriophages, wherein each light region of interest indicates a sensitivity of the bacterial strain to the viral strain of the bacteriophages; or dark regions of interest, wherein each dark region of interest corresponds to a development of bacteria in the presence of bacteriophages, wherein each dark region of interest indicates an insensitivity or a low sensitivity of the bacterial strain of interest to the viral strain of the bacteriophages.

11. The method according to claim 10, wherein a) comprises depositing a plurality of droplets spaced apart from one another, wherein at least two different droplets comprise:

bacteria of various bacterial strains; and/or various concentrations of bacteria of the same bacterial strain; or a combination thereof.

12. The method according to claim 1, wherein the sample is divided into various spatial regions that are separated from one another wherein:

at least two different spatial regions respectively comprise the same bacterial strain and different concentrations of bacteriophages of the same viral strain, respectively;

at least two different spatial regions respectively comprise the same bacterial strain and bacteriophages of various viral strains;

at least two different spatial regions respectively comprise bacteriophages of the same viral strain and various bacterial strains; or a combination thereof;

wherein each spatial region is associated with one region of interest of each acquired image, wherein two different spatial regions are associated with two different regions of interest of each acquired image, and wherein an analysis of at least one acquired image provides information on the sensitivity of a bacterial strain to a viral strain of bacteriophages in various spatial regions; and wherein the sample is distributed between various fluidic chambers of a fluidic chip, wherein each fluidic chamber corresponds to one spatial region of the sample.

13. The method according to claim 12, wherein the sample comprises more than ten different spatial regions that are separate from one another, wherein each spatial region is parameterized by three parameters corresponding to the bacterial strain of interest, to the viral strain of the bacteriophages and to the concentration of the bacteriophages, wherein at least one parameter of two different spatial regions is different.

14. The method according to claim 12, further comprising enriching prior to a), the enriching comprises:
   mixing bacteriophages of the same viral strain, or of various viral strains, in an aqueous solution comprising at least one strain of bacteria, thereby forming a mixture;
   incubating the mixture;
   filtering the mixture to retain the bacteria, and obtaining a solution enriched with bacteriophages; and
   using in a) the solution enriched in bacteriophages when bringing bacteria into contact with bacteriophages.

15. The method according to claim 1, wherein the sample is divided into various spatial regions that are separated from one another wherein:
   at least two different spatial regions respectively comprise the same bacterial strain and different concentrations of bacteriophages of the same viral strain, respectively;
   at least two different spatial regions respectively comprise the same bacterial strain and bacteriophages of various viral strains;
   at least two different spatial regions respectively comprise bacteriophages of the same viral strain and various bacterial strains; or
   a combination thereof;
   wherein each spatial region is associated with one region of interest of each acquired image, wherein two different spatial regions are associated with two different regions of interest of each acquired image, and wherein an analysis of at least one acquired image provides information on the sensitivity of a bacterial strain to a viral strain of bacteriophages in various spatial regions;
   wherein in a), the bacteria are located in the first agar medium, and the bacteriophages are located in a second solution, wherein a) further comprises depositing at least one droplet of the second solution on the first agar medium; and
   wherein the sample is formed following a deposition of the droplets of the second solution on the surface of the first agar medium in various positions, wherein the droplets are spaced apart from one another, such that one spatial region is defined by each droplet position.

16. The method according to claim 1, wherein the sample is divided into various spatial regions that are separated from one another wherein:
   at least two different spatial regions respectively comprise the same bacterial strain and different concentrations of bacteriophages of the same viral strain, respectively;
   at least two different spatial regions respectively comprise the same bacterial strain and bacteriophages of various viral strains;
   at least two different spatial regions respectively comprise bacteriophages of the same viral strain and various bacterial strains; or
   a combination thereof;
   wherein each spatial region is associated with one region of interest of each acquired image, wherein two different spatial regions are associated with two different regions of interest of each acquired image, and wherein an analysis of at least one acquired image provides information on the sensitivity of a bacterial strain to a viral strain of bacteriophages in various spatial regions;
   wherein in a), the bacteriophages are located in a second agar medium, and the bacteria are located in the first liquid medium a, wherein a) further comprises depositing a droplet of the first liquid medium on the second agar medium; and
   wherein the sample is formed following a deposition of the droplets of the first liquid medium the surface of the second agar medium in various positions, wherein the droplets are spaced apart from one another, such that one spatial region is defined by each droplet position.

\* \* \* \* \*